United States Patent
Shutt et al.

(10) Patent No.: US 7,358,410 B2
(45) Date of Patent: Apr. 15, 2008

(54) PROCESSES FOR FORMING POLYPROPYLENE FROM AN OXYGENATE-CONTAMINATED MONOMER FEEDSTOCK

(75) Inventors: John Richard Shutt, Merchtem (BE); Jeffrey L. Brinen, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 445 days.

(21) Appl. No.: 11/090,880

(22) Filed: Mar. 25, 2005

(65) Prior Publication Data

US 2006/0149103 A1 Jul. 6, 2006

Related U.S. Application Data

(60) Provisional application No. 60/640,578, filed on Dec. 30, 2004.

(51) Int. Cl.
*C07C 1/00* (2006.01)
*C07C 2/00* (2006.01)
*C07C 4/00* (2006.01)
*C07C 5/00* (2006.01)
*C07C 6/00* (2006.01)

(52) U.S. Cl. .............. 585/327; 585/326; 585/329; 526/943

(58) Field of Classification Search ........... 585/326, 585/327, 329; 526/943
See application file for complete search history.

(56) References Cited

U.S. PATENT DOCUMENTS

| | | | |
|---|---|---|---|
| 5,324,800 A | 6/1994 | Welborn, Jr. et al. | 526/160 |
| 6,121,503 A | 9/2000 | Janssen et al. | 585/640 |
| 6,399,535 B1 * | 6/2002 | Shih et al. | 502/167 |
| 6,492,293 B1 | 12/2002 | Speakman | |
| 2003/0045761 A1 | 3/2003 | Kuechler et al. | |
| 2003/0199721 A1 | 10/2003 | Ding et al. | 585/807 |
| 2003/0199724 A1 | 10/2003 | Van Egmond et al. | 585/899 |
| 2004/0076554 A1 | 4/2004 | Kuechler et al. | 422/139 |
| 2004/0176646 A1 | 9/2004 | Van Egmond et al. | 568/699 |
| 2005/0033013 A1 | 2/2005 | Van Egmond et al. | 528/392 |
| 2005/0033103 A1 | 2/2005 | Van Egmond et al. | 585/800 |

FOREIGN PATENT DOCUMENTS

| | | |
|---|---|---|
| WO | WO 01/64340 | 9/2001 |
| WO | WO 2004/007509 | 1/2004 |

OTHER PUBLICATIONS

United States Application filed Jan. 25, 2005, "Catalyst Composition And Use Thereof", Inventors: Gregory A. Solan and Christopher J. Davies.

(Continued)

*Primary Examiner*—Walter D. Griffin
*Assistant Examiner*—Lessanework T Seifu

(57) ABSTRACT

The present invention provides various processes for producing polypropylene from an oxygenate-contaminated propylene-containing feedstock, preferably derived from an oxygenate to olefin reaction system. In one embodiment, the process includes providing a propylene-containing stream from an oxygenate to olefin reaction system, wherein the propylene-containing stream comprises propylene and an oxygenate. The propylene in the propylene-containing stream contacts a polymerization catalyst in a polymerization zone under conditions effective to polymerize the propylene to form the polypropylene.

25 Claims, 1 Drawing Sheet

OTHER PUBLICATIONS

U.S. Appl. No. 60/553,839, filed Mar. 17, 2004, "Catalyst Composition And Use Thereof", Inventors: Gregory A. Solan and Christopher J. Davies.

U.S. Appl. No. 60/581,580, filed Jun. 21, 2004, "Polymerization Process", Inventors: Robert Olds Hagerty, Chia S. Chee, Randall B. Laird, Michael A. Risch, Pradeep P. Shirodkar, Peijun Jiang.

U.S. Appl. No. 09/564,613, filed May 4, 2000, "Multiple Riser Reactor", Inventors: James Lattner, Jeffrey S. Smith, Nicolas Coute, Keith Kuechler.

U.S. Appl. No. 10/786,988, filed Feb. 25, 2004, "Process Of Making Polypropylene From Intermediate Grade Propylene", Inventors: Cor F. van Egmond and Lawrence C. Smith.

Johnston et al, "Copolymerization of Ethylene and Propylene with Functionalized Vinyl Monomers by Palladium (II) Catalysts," J. Am. Chem. Soc., vol. 118, pp. 267-268 (1996).

Rix & Brookhart, "Energetics of Migratory Insertion Reactions in Pd (II) Acyl Ethylene, Alkyl Ethylene, and Alkyl Carbonyl Complexes," J. Am. Chem. Soc., vol. 117, pp. 1137-1138.

Schmidt & Brookhart, "Implications of Three-Center, Two-Electron M-H-C Bonding for Related Alkyl Migration Reactions: Design and Study of an Ethylene Polymerization Catalyst," J. Am. Chem. Soc., vol. 107, pp. 1443-1444 (1985).

Younkin et al, "Neutral, Single-Component Nickel (II) Polyolefin Catalysts That Tolerate Heteroatoms," Science, vol. 287, pp. 460-462, Jan. 21, 2000.

* cited by examiner

_US 7,358,410 B2_

PROCESSES FOR FORMING POLYPROPYLENE FROM AN OXYGENATE-CONTAMINATED MONOMER FEEDSTOCK

CROSS REFERENCE TO RELATED APPLICATIONS

This application claims the benefit of Provisional Application No. 60/640,578 filed Dec. 30, 2004, the disclosure of which is fully incorporated herein by reference.

FIELD OF THE INVENTION

The present invention relates to processes for forming polypropylene. More particularly, the present invention relates to processes for forming polypropylene from a contaminated feedstock comprising propylene and one or more oxygenates.

BACKGROUND OF THE INVENTION

Propylene is an important commodity petrochemical useful in a variety of processes for making plastics and other chemical compounds. For example, propylene is used to make various polypropylene plastics, and in making other chemicals such as acrylonitrile and propylene oxide.

The petrochemical industry has known for some time that oxygenates, especially alcohols, are convertible into light olefins, such as propylene. The preferred conversion process is generally referred to as an oxygenate-to-olefin (OTO) or specifically as a methanol-to-olefins (MTO) process, where methanol is converted to primarily ethylene and/or propylene in the presence of a molecular sieve catalyst.

Various byproducts are produced in the OTO reaction process. Some of these byproducts should be separated from the propylene product in order to provide propylene suitable for polymerization disposition. These byproducts may include components that are heavier than propane and propylene, such as C4+ components (olefinic and aliphatic) as well as multiply unsaturated components such as acetylene, methyl acetylene and propadiene.

Additionally, oxygenate compounds such as alcohols, aldehydes, ketones, esters, acids and ethers (particularly dimethyl ether "DME") in the C1 to C6 range as well as trace quantities of aromatic compounds may be formed in OTO reactors or in OTO effluent processing. A small amount of oxygenate from the feedstock, e.g., methanol and/or DME, can pass through the OTO reactor with the product effluent without being converted to the desired product. As a result of oxygenate synthesis and/or incomplete oxygenate conversion in an OTO reactor system, an effluent from an OTO reactor can contain undesirably high concentrations of oxygenate compounds. These oxygenates, particularly light oxygenates, are in amounts that would make the propylene off-specification for its preferred disposition, e.g., polymerization.

Conventional propylene production facilities that produce propylene for polymerization disposition are required by the industry to produce very pure propylene. Conventional polymerization grade propylene contains at least 99.5 weight percent propylene, with the balance being mostly propane. A minor amount of other contaminants such as hydrogen, oxygen, and water, typically on a wppm level, may be tolerated in polymerization grade propylene. The high purity requirements in the industry are directly related to the usage of high activity catalysts for the formation of polypropylene. For example, bulky ligand metallocene-type catalyst systems such as those described in, for example, U.S. Pat. No. 5,324,800, are highly sensitive to oxygen, ethers, ketones, aldehydes, carbon dioxide, and other contaminants.

As a result of the high purity propylene requirements, various processing schemes have been developed for separating one or more contaminants from propylene-containing effluent streams. For example, U.S. Pat. No. 6,121,503 to Janssen et al., the entirety of which is incorporated herein by reference, discloses a process for converting an oxygenate feed to high purity olefins such as polymer-grade propylene.

The equipment count and resources necessary for processing crude propylene product streams and for providing high purity polymerization grade propylene can substantially increase both investment and operating costs. Thus, the need exists for the ability to polymerize propylene derived from a propylene-containing stream that also contains a certain level of impurities, e.g., byproducts of the OTO reaction process.

SUMMARY OF THE INVENTION

In one embodiment, the invention is to a process for producing polypropylene, wherein the process comprises the steps of: (a) providing a propylene-containing stream from an oxygenate to olefin reaction system, wherein the propylene-containing stream comprises propylene and an oxygenate; (b) directing the propylene-containing stream to a polymerization zone; and (c) contacting the propylene in the propylene-containing stream with a polymerization catalyst in the polymerization zone under conditions effective to polymerize the propylene to form the polypropylene.

In another embodiment, the present invention is directed to a process for producing a polymer, wherein the process comprises the steps of: (a) contacting an oxygenate with a molecular sieve catalyst composition in an oxygenate to olefins reaction system under first conditions effective to form an initial product stream comprising ethylene, propylene and an oxygenate; (b) separating the initial product stream into an ethylene-containing stream and a propylene-containing stream, wherein the ethylene-containing stream comprises a weight majority of the ethylene from the initial product stream, and wherein the propylene-containing stream comprises a weight majority of the propylene from the initial product stream and at least a portion of the oxygenate; (c) directing the propylene-containing stream to a polymerization zone; and (d) contacting the propylene in the propylene-containing stream with a polymerization catalyst in the polymerization zone under second conditions effective to form the polymer.

Optionally, the polymerization catalyst comprises a metal complex comprising a metal, which optionally is activated by an activator. The activator optionally is selected from the group consisting of methyl alumoxane (MAO), and a perfluoro tetraphenylborate salt. The metal complex also preferably comprises a tridentate ligand, preferably a tridentate ligand comprising three nitrogen atoms, which coordinate with the metal. In this aspect of the invention, at least one of the nitrogen atoms optionally is bonded to a 2,6-diisopropyl phenyl substituent. In another aspect of the invention, the tridentate ligand comprises two nitrogen atoms and one oxygen atom, and the two nitrogen atoms and the oxygen atom coordinate with the metal. In this embodiment, at least one of the nitrogen atoms preferably is bonded to a 2,6-diisopropyl phenyl substituent. Optionally, the metal is selected from Group 6, 7, 8, 9, 10 or 11 of the Periodic Table of the Elements. For example, the metal optionally is selected from Group 8, 9 or 10. In another embodiment, the metal is selected from Group 9, 10 or 11. Optionally, the metal is selected from the group consisting of iron, ruthenium, osmium, hassium, cobalt, rhodium, iridium, meitnerium, nickel, palladium, platinum and darmstadtium. Alternatively, the metal is selected from the group consisting of iron, cobalt and nickel. Alternatively, the metal is selected from the group consisting of nickel and palladium. Optionally, the metal complex is dispersed in water.

Optionally, the oxygenate comprises one or more of methanol, ethanol, dimethyl ether, ethanal, propanal, acetone, isopropyl alcohol and mixtures thereof. Optionally, the propylene-containing stream comprises at least about 1 wppm, at least about 10 wppm, at least about 100 wppm, at least about 1,000 wppm, at least about 1 weight percent, at least about 2 weight percent, at least about 5 weight percent, from about 10 wppm to about 10 weight percent, or less than about 10 weight percent oxygenates, based on the total weight of the propylene-containing stream. Optionally, the propylene-containing stream comprises less than about 5 wppm water, based on the total weight of the propylene-containing stream. Optionally, the propylene-containing stream is derived from an initial product stream comprising ethylene, propylene, water and the oxygenate.

BRIEF DESCRIPTION OF THE FIGURE

The present invention will be better understood with reference to non-limiting FIG. 1, which presents a flow diagram of an oxygenate to olefin reaction system.

DETAILED DESCRIPTION OF THE INVENTION

A. Introduction

Figure 1:
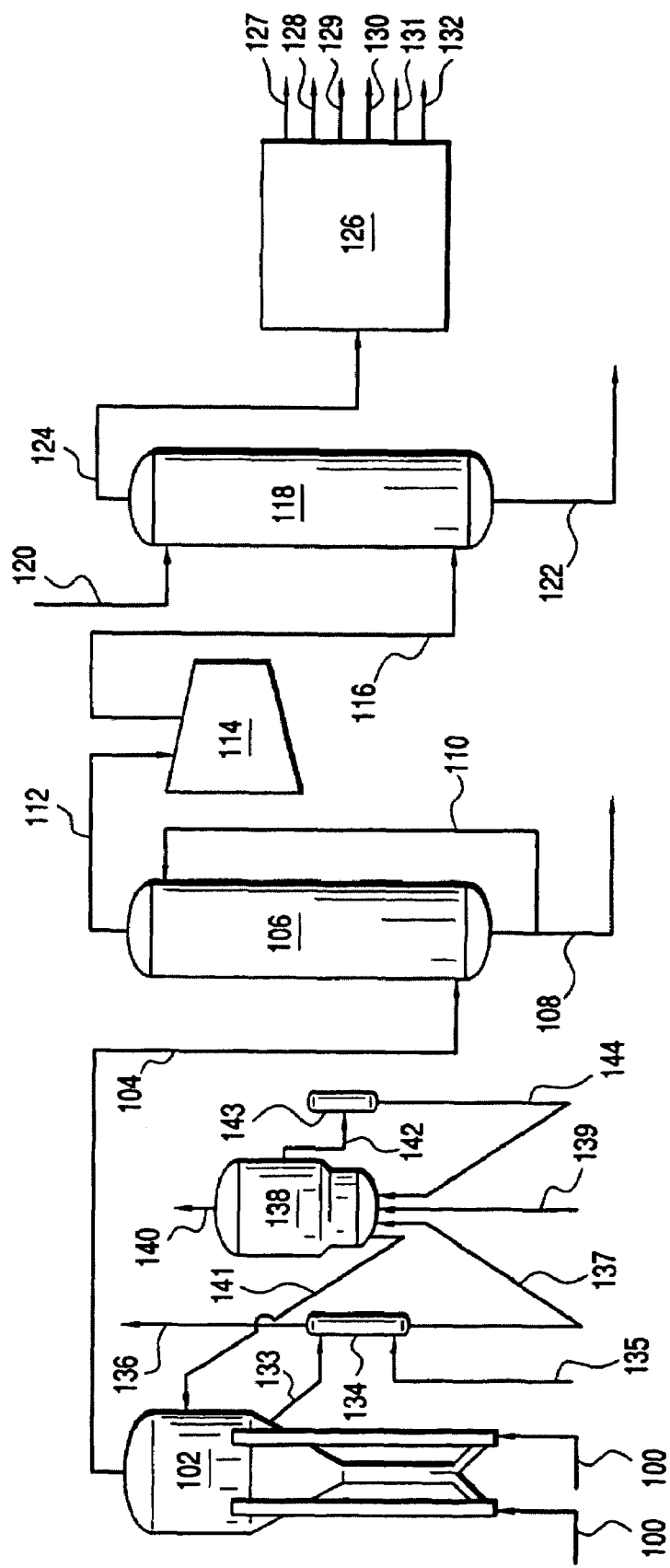

The present invention provides various processes for producing polypropylene from an oxygenate-contaminated propylene-containing feedstock, preferably derived from an oxygenate to olefin (OTO) reaction system. In one embodiment, the process includes the step of providing a propylene-containing stream from an OTO reaction system, wherein the propylene-containing stream comprises propylene and an oxygenate. The propylene in the propylene-containing stream contacts a polymerization catalyst in a polymerization zone under conditions effective to polymerize the propylene to form the polypropylene.

As used herein, an "oxygenate" or "oxygenated compound" is a molecule containing at least one oxygen atom, at least one carbon atom and at least two hydrogen atoms. A non-limiting list of exemplary oxygenates includes: formaldehyde, ethanal, propanal, butanal, pentanal and higher aldehydes; acetone, butanone, pentanone, hexanone and higher ketones; dimethyl ether, methyl ethyl ether, diethyl ether, ethyl propyl ether and higher ethers; unsaturated species thereof, e.g., crotonaldehyde; formic acid, acetic acid, propionic acid, butanoic acid and higher carboxylic acids.

B. Oxygenate to Olefin Reaction Systems

As indicated above, the present invention is directed to converting propylene in a propylene-containing stream, which also comprises an oxygenate. The preferred propylene containing composition is derived from an OTO reaction process, which will now be described in greater detail. As used herein, "reaction system" means a system comprising a reactor, optionally a catalyst cooler, optionally a catalyst regenerator, optionally a catalyst stripper, and optionally an effluent processing system for separating the various components contained in an OTO reaction effluent formed by the OTO reaction process. The reactor comprises a reaction unit, which defines a reaction zone, and optionally a disengaging unit, which defines a disengaging zone.

In an OTO reaction system, a molecular sieve catalyst composition is used to convert an oxygenate-containing feedstock to light olefins. Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. The molecular sieve catalyst composition fluidized according to the present invention optionally comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof. Additionally or alternatively, the molecular sieve comprises an aluminophosphate (ALPO) molecular sieve. Preferred ALPO molecular sieves include ALPO-5, ALPO-11, ALPO-18, ALPO-31, ALPO-34, ALPO-36, ALPO-37, ALPO-46, AEI/CHA intergrowths, mixtures thereof, and metal containing forms thereof Ideally, the catalyst to be fluidized according to the present invention is selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, a zeolitic molecular sieve, ZSM-34, ZSM-5, metal containing forms thereof, intergrown forms thereof, AEI/CHA intergrowths, and mixtures thereof.

The oxygenate-containing feedstock that is directed to an OTO reaction system optionally contains one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and more preferably from 1 to 4 carbon atoms, and most preferably methanol.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more organic compounds containing at least one oxygen atom. In the most preferred embodiment of the process of invention, the oxygenate in the feedstock comprises one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock comprises one or more of methanol, ethanol, DME, diethyl ether or a combination thereof.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In a preferred embodiment, the feedstock, which ideally comprises methanol, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as an oxygenate-to-olefins (OTO) reaction process. In an OTO process, typically an oxygenated feedstock, most preferably a methanol- and ethanol-containing feedstock, is converted in the presence of a molecular sieve catalyst composition into one or more olefins, preferably and predominantly, ethylene and/or propylene, referred to herein as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone.

The WHSV is maintained at a level sufficient to keep the catalyst composition in a fluidized state within a reactor.

Typically, the WHSV ranges from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of a feedstock containing methanol, DME, or both, is in the range of from about 20 hr$^{-1}$ to about 300 hr$^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

FIG. 1 illustrates a non-limiting exemplary OTO reaction system. In the figure, an oxygenate-containing feedstock is directed through lines 100 to an OTO fluidized reactor 102 wherein the oxygenate (preferably comprising methanol) in the oxygenate-containing feedstock contacts a molecular sieve catalyst composition under conditions effective to convert the oxygenate to light olefins and various byproducts, which are yielded from the fluidized reactor 102 in an olefin-containing stream in line 104. The olefin-containing stream in line 104 optionally comprises methane, ethylene, ethane, propylene, propane, various oxygenate byproducts, C4+ olefins, water and hydrocarbon components. The olefin-containing stream in line 104 is directed to a quench unit or quench tower 106 wherein the olefin-containing stream in line 104 is cooled and water and other readily condensable components are condensed.

The condensed components, which comprise water, are withdrawn from the quench tower 106 through a bottoms line 108. A portion of the condensed components are recycled through line 110 back to the top of the quench tower 106. The components in line 110 preferably are cooled in a cooling unit, e.g., heat exchanger (not shown), so as to provide a cooling medium to cool the components in quench tower 106.

An olefin-containing vapor is yielded from the quench tower 106 through overhead stream 112. The olefin-containing vapor is compressed in one or more compressors 114 and the resulting compressed olefin-containing stream is optionally passed through line 116 to a water absorption unit 118. Methanol is preferably used as the water absorbent, and is fed to the top portion of the water absorption unit 118 through line 120. Methanol and entrained water, as well as some oxygenates, are separated as a bottoms stream through line 122. The light olefins are recovered through an overhead effluent stream 124, which comprises light olefins. Optionally, the effluent stream 124 is sent to an additional compressor or compressors, not shown, and a heat exchanger, not shown. Ultimately, the effluent stream 124 is directed to separation system 126, which optionally comprises one or more separation units such as $CO_2$ removal unit(s) (e.g., caustic tower(s)), distillation columns, absorption units, and/or adsorption units.

The separation system 126 separates the components contained in the overhead line 124. Thus, separation system 126 forms a light ends stream 127, optionally comprising methane, hydrogen and/or carbon monoxide; an ethylene-containing stream 128 comprising mostly ethylene; an ethane-containing stream 129 comprising mostly ethane; a propylene-containing stream 130 comprising mostly propylene; a propane-containing stream 131 comprising mostly propane; and one or more byproduct streams, shown as line 132, comprising one or more of the oxygenate byproducts, provided above, heavy olefins, heavy paraffins, and/or absorption mediums utilized in the separation process. Preferably, the propylene-containing stream 130 is directed to polymerization disposition according to the processes of the present invention. Accordingly, the propylene-containing stream 130 comprises at least some residual oxygenate contaminants. Separation processes that may be utilized to form these streams are well-known and are described, for example, in pending U.S. patent application Ser. No. 10/124,859 filed Apr. 18, 2002; Ser. No. 10/125,138 filed Apr. 18, 2002; Ser. No. 10/383,204 filed Mar. 6, 2003; Ser. No. 10/635,410 filed Aug. 6, 2003; Ser. No. 10/635,401 filed Aug. 6, 2004; Ser. No. 10/786,988 filed on Feb. 25, 2004; and Ser. No. 10/805,983 filed Mar. 22, 2004, the entireties of which are incorporated herein by reference.

FIG. 1 also illustrates a catalyst regeneration system, which is in fluid communication with fluidized reactor 102. As shown, at least a portion of the catalyst compositions contained in fluidized reactor 102 are withdrawn and transported, preferably in a fluidized manner, in conduit 133 from the fluidized reactor 102 to a catalyst stripper 134. In the catalyst stripper 134, the catalyst compositions contact a stripping medium, e.g., steam and/or nitrogen, under conditions effective to remove interstitial hydrocarbons from the molecular sieve catalyst compositions. As shown, stripping medium is introduced into catalyst stripper 134 through line 135, and the resulting stripped stream 136 is released from catalyst stripper 134. Optionally, all or a portion of stripped stream 136 is directed back to fluidized reactor 102.

During contacting of the oxygenate feedstock with the molecular sieve catalyst composition in the fluidized reactor 102, the molecular sieve catalyst composition may become at least partially deactivated. That is, the molecular sieve catalyst composition becomes at least partially coked. In order to reactivate the molecular sieve catalyst composition, the catalyst composition preferably is directed to a catalyst regenerator 138. As shown, the stripped catalyst composition is transported, preferably in the fluidized manner, from catalyst stripper 134 to catalyst regenerator 138 in conduit 137. Preferably, the stripped catalyst composition is transported in a fluidized manner through conduit 137.

In catalyst regenerator 138, the stripped catalyst composition contacts a regeneration medium, preferably comprising oxygen, under conditions effective (preferably including heating the coked catalyst) to at least partially regenerate the catalyst composition contained therein. As shown, the regeneration medium is introduced into the catalyst regenerator 138 through line 139, and the resulting regenerated catalyst compositions are ultimately transported, preferably in a fluidized manner, from catalyst regenerator 138 back to the fluidized reactor 102 through conduit 141. The gaseous combustion products are released from the catalyst regenerator 138 through flue gas stream 140. In another embodiment, not shown, the regenerated catalyst composition additionally or alternatively is directed, optionally in a fluidized manner, from the catalyst regenerator 138 to one or more of the fluidized reactor 102 and/or the catalyst stripper 134. In one embodiment, not shown, a portion of the catalyst composition in the reaction system is transported directly, e.g., without first passing through the catalyst stripper 134, optionally in a fluidized manner, from the fluidized reactor 102 to the catalyst regenerator 138.

As the catalyst compositions contact the regeneration medium in catalyst regenerator 138, the temperature of the catalyst composition will increase due to the exothermic nature of the regeneration process. As a result, it is desirable to control the temperature of the catalyst composition by directing at least a portion of the catalyst composition from the catalyst regenerator 138 to a catalyst cooler 143. As shown, the catalyst composition is transported in a fluidized manner from catalyst regenerator 138 to the catalyst cooler 143 through conduit 142. The resulting cooled catalyst composition is transported, preferably in a fluidized manner from catalyst cooler 143 back to the catalyst regenerator 138 through conduit 144. In another embodiment, not shown, the cooled catalyst composition additionally or alternatively is directed, optionally in a fluidized manner, from the catalyst cooler 143 to one or more of the fluidized reactor 102 and/or the catalyst stripper 134.

C. The Propylene-Containing Stream

The precise composition of the propylene-containing stream that is directed to polymerization disposition may vary widely. Preferably, the propylene-containing stream is derived from an OTO reaction system. Several preferred propylene containing compositions are described, for example, in U.S. patent applications Ser. No. 10/635,401 filed Aug. 6, 2003; Ser. No. 10/786,988 filed on Feb. 25, 2004; and Ser. No. 10/805,983 filed Mar. 22, 2004, the entireties of which are incorporated herein by reference.

In one embodiment, the propylene-containing stream that is directed to polymerization disposition according to the present invention comprises at least 95 volume percent propylene, at least 0.5 volume percent propane, at least 10 vppm ethane, at least 1 vppm ethylene, and from 0.5 to 2 vppm dimethyl ether. It has been discovered that dimethyl ether, in the amounts found in the propylene-containing stream of the present invention, is not significantly detrimental to several polymerization catalysts, described in detail below.

Optionally, the propylene-containing stream includes additional contaminants. A non-limiting list of additional possible contaminants that may be present in the propylene-containing stream of the present invention, includes one or more of acetylene, methyl acetylene, propadiene, C4+ hydrocarbons, methanol, water and hydrogen. Specifically, the propylene-containing stream of the present invention optionally comprises at least 0.05 vppm acetylene, or from 1 to 2 vppm acetylene. Optionally, the propylene-containing stream further comprises at least 0.01 vppm methyl acetylene, or from 1 to 3 vppm methyl acetylene. Optionally, the propylene-containing stream further comprises at least 0.01 vppm propadiene, or from 1 to 3 vppm propadiene. Optionally, the propylene-containing stream further comprises at least 0.02 vppm C4+ hydrocarbons, or from 5 to 15 vppm C4+ hydrocarbons. Optionally, the propylene-containing stream further comprises at least 0.01 vppm methanol, or from 0.5 to 1 vppm methanol. Optionally, the propylene containing composition further comprises at least 0.01 vppm water, or from 1 to 5 vppm water. Optionally, the propylene-containing stream further comprises at least 0.01 vppm hydrogen, or from 5 to 20 vppm hydrogen. Optionally, the propylene-containing stream comprises from 0.5 to 2 vppm methanol. Optionally, the propylene-containing stream comprises from 2 to about 5 volume percent propane. Optionally, the propylene-containing stream comprises from 300 to 1,000 vppm ethane. Optionally, the propylene-containing stream comprises from 5 to 15 vppm ethylene. Optionally, the propylene-containing stream comprises from 0.5 to 1 vppm dimethyl ether, or from 1 to 2 vppm dimethyl ether. Preferably, the propylene-containing stream is depleted, or substantially depleted, of arsine and phosphine. In one embodiment, the propylene-containing stream comprises less than 0.01 vppm arsine, preferably less than 0.001 vppm arsine. Preferably, the propylene-containing stream comprises less than 0.01 vppm phosphine, more preferably less than 0.001 vppm phosphine.

In another embodiment of the present invention, the propylene-containing stream comprises at least 95 volume percent propylene, from 0.5 to about 5 volume percent propane, at least 0.02 vppm C4+ hydrocarbons, at least 0.01 vppm methanol, and from 0.5 vppm to 2 vppm dimethyl ether. Optionally, the propylene-containing stream of this embodiment further comprises one or more of ethane, ethylene, propane, arsine, phosphine, acetylene, methyl acetylene, water, hydrogen and/or propadiene, optionally in the amounts provided in the above ranges.

In another embodiment, the present invention provides a propylene-containing stream comprising at least 95 volume percent propylene, from 0.5 to 5 volume percent propane, at least 10 vppm ethane, at least 0.05 vppm acetylene, and from 0.5 to 2 vppm dimethyl ether. Optionally, the propylene-containing stream of this embodiment further comprises one or more of ethylene, C4+ hydrocarbons, methanol, arsine, phosphine, methyl acetylene, water, hydrogen and/or propadiene, optionally in the amounts provided in the above ranges.

In another embodiment, the present invention is directed to a propylene-containing stream comprising at least 95 volume percent propylene, from 0.5 to about 5 volume percent propylene, at least 10 vppm ethane, at least 0.02 vppm C4+ hydrocarbons, and from 0.5 to 2 vppm dimethyl ether. Optionally, the propylene-containing stream of this embodiment further comprises one or more of ethylene, acetylene, methanol, arsine, phosphine, methyl acetylene, water, hydrogen and/or propadiene, optionally in the amounts provided in the above ranges.

In another embodiment, the present invention is directed to a propylene-containing stream comprising at least 95 volume percent propylene, from 0.5 to 5 volume percent propane, at least 0.1 vppm water, at least 0.01 vppm methanol, and from 0.5 to 2 vppm dimethyl ether. Optionally, the propylene-containing stream of this embodiment further comprises one or more of ethane, ethylene, C4+ hydrocarbons, acetylene, arsine, phosphine, methyl acetylene, hydrogen and/or propadiene, optionally in the amounts provided in the above ranges.

In another embodiment, the present invention is directed to a propylene-containing stream, wherein the composition is formed by a specified process. The process preferably includes a step of contacting an oxygenate with a molecular sieve catalyst in a reactor under conditions effective to form an effluent stream comprising propylene, propane, ethylene, dimethyl ether and ethane. The effluent stream is separated in a first separation unit into a first fraction and a second fraction. The first fraction contains a majority of the ethane, ethylene and propylene, and the second fraction contains a majority of the dimethyl ether. At least a portion of the first fraction is separated into a third fraction and the propylene-containing stream. The third fraction contains the majority of the ethylene and ethane in the at least a portion of the first fraction. The propylene-containing stream comprises at least 95 volume percent propylene, at least 0.5 volume percent propane, at least 10 vppm ethane, at least 1 vppm ethylene and from 0.5 to 2 vppm dimethyl ether. In this embodiment, the conditions in the contacting step optionally provide for 95 to 97 weight percent conversion of the oxygenate, based on the total weight of the oxygenate fed to the reactor. The contacting optionally occurs at a pressure of at least 150 psig, a pressure of from 150 to 370 psig, or a pressure of from 250 to 370 psig.

In another embodiment, the present invention is directed to a propylene-containing stream, which is formed by a process comprising an initial C2/C3 separation step. This process also comprises a step of contacting an oxygenate with a molecular sieve catalyst in a reactor under conditions effective to form an effluent stream comprising propylene, propane, ethylene, DME and ethane. The effluent stream is separated in a first separation unit into a first fraction and a second fraction. In this process, the first fraction contains a majority of the ethane and ethylene and, the second fraction contains a majority of the DME, propane and propylene. At least a portion of the second fraction is separated into the propylene-containing stream and a third fraction. In this embodiment, the propylene-containing stream comprises at least 95 volume percent propylene, at least 0.5 volume percent propane, at least 10 vppm ethane, at least 1 vppm ethylene, and from 0.5 to 2 vppm DME. The third fraction contains a majority of the propane and DME present in the at least a portion of the second fraction.

D. Polymerization Processes

The propylene-containing stream, described above, is particularly well-suited for polymerization over certain catalyst compositions to form plastic compositions, e.g., polyolefins, particularly polypropylene. A preferred polymerization system for use in the present invention is disclosed in U.S. Provisional Patent Application Ser. No. 60/581,580 filed on Jun. 21, 2004, the entirety of which is incorporated herein by reference. Optionally, the catalyst comprises a metallocene, Ziegler/Natta, aluminum oxide or an acid catalytic system. See, for example, U.S. Pat. Nos. 3,258,455; 3,305,538; 3,364,190; 5,892,079; 4,659,685; 4,076,698; 3,645,992; 4,302,565; and 4,243,691, the entireties of which are incorporated herein by reference. In general, these methods involve contacting the propylene product with a polymerization catalyst (e.g., a polypropylene-forming catalyst) at a pressure and temperature effective to form the polypropylene product. Metallocene and Ziegler/Natta catalyst systems may have limitations when implemented in the processes of the present invention, however, due to their sensitivity to the one or more oxygenates contained in the propylene-containing stream described above.

Desirably, the polypropylene forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

Any conventional reactor type may be used for the polymerization process of this invention. Non-limiting examples include fluid bed reactors, slurry reactors, or linear flow reactors. The use of a fluid bed reactor is described in U.S. Pat. No. 4,482,687, the reactor and catalyst description expressly being incorporated herein. The use of a linear flow loop type reactor is disclosed in U.S. Pat. No. 5,684,097, the reactor and catalyst description being expressly incorporated herein.

In a fluid bed process, solid polymer powder is maintained in a fluidized state by passing a stream of reaction gas up from the base of a reactor, where the reaction gas comprises olefin monomer. The reaction gas is withdrawn from the top of the reactor cooled and then recycled back to the base of the reactor. Solid polymer is removed as it builds up at the base of the reactor. A high rate of reaction gas recycle is typically required to achieve fluidization. Generally the recycle rate is about 50 times the rate of a stream of new olefin gas feed to the column. The new olefin gas stream is fed to the column at a rate equal to the withdraw of polyolefin product and any purge stream.

A loop reactor is a preferred form of a linear flow reactor. In a loop reactor, long straight lengths of tubing are interjected with short bends forming a loop. Monomer(s), catalyst, and, optionally, solvent are charged into the loop forming a slurry. Polymer formed in the loop is removed from the reactor along with unreacted monomer and diluent or solvent. Multiple loops may be used with portions of the slurry from the first reactor withdrawn and added to a second loop reactor.

In one embodiment, the invention is to a process for producing polypropylene. The process preferably includes the step of providing a propylene-containing stream from an OTO reaction system, wherein the propylene-containing stream comprises propylene and an oxygenate. The propylene-containing stream is directed to a polymerization zone. In the polymerization zone, the propylene in the propylene-containing stream contacts a polymerization catalyst under conditions effective to polymerize the propylene to form the polypropylene.

In another embodiment, the process comprises the step of contacting an oxygenate with a molecular sieve catalyst composition in an oxygenate to olefins reaction system under first conditions effective to form an initial product stream comprising ethylene, propylene and an oxygenate. The initial product stream is separated into an ethylene-containing stream and a propylene-containing stream. In this embodiment, the ethylene-containing stream comprises a weight majority of the ethylene from the initial product stream, and the propylene-containing stream comprises a weight majority of the propylene from the initial product stream and at least a portion of the oxygenate. The propylene-containing stream is then directed to a polymerization zone, in which the propylene in the propylene-containing stream contacts a polymerization catalyst under second conditions effective to form the polymer.

Optionally, the oxygenate in the propylene-containing stream comprises one or more of methanol, ethanol, dimethyl ether, ethanal, propanal, acetone, isopropyl alcohol and mixtures thereof. Optionally, the propylene-containing stream comprises at least about 1 wppm, at least about 10 wppm, at least about 100 wppm, at least about 1,000 wppm at least about 1 weight percent, at least about 2 weight percent, at least about 5 weight percent, from about 10 wppm to about 10 weight percent, or less than about 10 weight percent oxygenates, based on the total weight of the propylene-containing stream. Optionally, the propylene-containing stream comprises less than about 5 wppm water, based on the total weight of the propylene-containing stream. Optionally, the propylene-containing stream is derived from an initial product stream comprising ethylene, propylene, water and the oxygenate.

E. Preferred Polymerization Catalyst Systems

1. Polymerization Catalysts

The present invention is directed toward contacting propylene in a propylene-containing feedstock with a polymerization catalyst under conditions effective to convert the propylene to polypropylene. The one or more oxygenates present in the propylene-containing feedstock may render the propylene-containing stream unsuitable for polymerization over certain polymerization catalysts. Accordingly, the polymerization processes of the present invention preferably occur over one or more specific polymerization catalysts, which are relatively insensitive to the oxygenate compositions(s) contained in the propylene-containing stream. As used herein, the term "polymerization catalyst" means a catalyst composition suitable for polymerizing and/or oligomerizing propylene, optionally with one or more co-monomers. Several particularly preferred polymerization catalysts are described in U.S. Provisional Patent Application Ser. No. 60/553,839 filed on Mar. 17, 2004, the entirety of which is incorporated herein by reference.

Optionally, the polymerization catalyst comprises a metal complex comprising a metal. The metal complex preferably comprises a tridentate ligand, preferably a tridentate ligand comprising three nitrogen atoms, which coordinate with the metal. In this aspect of the invention, at least one of the nitrogen atoms optionally is bonded to a 2,6-diisopropyl phenyl substituent. In another aspect of the invention, the tridentate ligand comprises two nitrogen atoms and one oxygen atom, and the two nitrogen atoms and the oxygen atom coordinate with the metal. In this embodiment, at least one of the nitrogen atoms preferably is bonded to a 2,6-diisopropyl phenyl substituent.

Optionally, the metal is selected from Group 6, 7, 8, 9, 10 or 11 of the Periodic Table of the Elements. For example, the metal optionally is selected from Group 8, 9 or 10. In another embodiment, the metal is selected from Group 9, 10 or 11. Optionally, the metal is selected from the group consisting of iron, ruthenium, osmium, hassium, cobalt, rhodium, iridium, meitnerium, nickel, palladium, platinum and darmstadtium. Alternatively, the metal is selected from the group consisting of iron, cobalt and nickel. Alternatively, the metal is selected from the group consisting of nickel and palladium.

Optionally, the metal complex is dispersed in water.

Optionally, the polymerization catalyst comprises a Group 9, 10 or 11 transition metal compound containing neutral, mono- or di-anionic tridentate nitrogen/oxygen based ligands that are useful, with or without activators, to polymerize olefins, particularly propylene and especially propylene contaminated with low levels of oxygenates derived from the OTO reaction process.

Optionally, the polymerization catalyst comprises a Group 9, 10 or 11 transition metal compound containing neutral, bidentate nitrogen/oxygen based ligands that are useful, with or without activators, to polymerize olefins, particularly propylene, and more particularly propylene in a propylene-containing stream that is contaminated with one or more oxygenated compounds.

Preferably, the polymerization catalyst utilized according to the present invention comprises a transition metal compound of the formula:

$$[LMX_w]_z$$

wherein:

w is 1, 2 or 3;

z is 1 or 2;

each M is, independently, a Group 9, 10 or 11 metal, preferably a Group 9, or 10 metal;

each L is, independently, a neutral, mono- or di-anionic tridentate ligand that is bonded to M by two nitrogen atoms and one oxygen atom, (where one of the nitrogen atoms and the oxygen atom are terminal atoms and the other nitrogen atom is a central atom), and the central nitrogen atom is part of a pyridinyl ring, and the central nitrogen atom is connected to the terminal oxygen atom at one ortho position of the pyridinyl ring via a group having at least two carbon atoms, and the central nitrogen atom is connected to the terminal nitrogen atom at the other ortho position of the pyridinyl ring via a group having at least one carbon atom (preferably at least two carbon atoms), and the terminal nitrogen atom is substituted with one $C_3$-$C_{50}$ hydrocarbyl or one hydrogen or substituted with one $C_3$-$C_{50}$ hydrocarbyl and one hydrogen atom or two hydrocarbyls wherein at least one hydrocarbyl is a $C_3$-$C_{50}$ hydrocarbyl, and the terminal oxygen atom is bonded to two different carbon atoms or one carbon atom and one hydrogen atom to give a neutral donor or one carbon atom to form a mono-anionic donor; and X is independently a monoanionic ligand.

The oligomerization or polymerization compositions of this invention also preferably comprises transition metal compounds of formula:

$$[LMX_w]_z$$

wherein:

w is 1, 2 or 3;

z is 1 or 2;

each M is, independently, a Group 9 to 11 metal, preferably a Group 9, or 10 metal;

each L is, independently, a neutral bidentate ligand that is bonded to M by two nitrogen atoms, (where one of the nitrogen atoms is a terminal atom and the other nitrogen atom is a central atom), and the central nitrogen atom is part of a pyridinyl ring and the central nitrogen atom is connected to the terminal nitrogen atom at one ortho position of the pyridinyl ring via a group having at least one carbon atom (preferably at least two carbon atoms), and the other ortho position of the pyridyl ring is substituted with a group represented by the formula —CR=CR—O—R, wherein each R is independently a C1 to C12 alkyl group, and the terminal nitrogen atom is substituted with one $C_3$-$C_{50}$ hydrocarbyl or one hydrogen or substituted with one $C_3$-$C_{50}$ hydrocarbyl and one hydrogen atom or two hydrocarbyls wherein at least one hydrocarbyl is a $C_3$-$C_{50}$ hydrocarbyl; and X is independently a monoanionic ligand.

In the formulae depicted throughout this specification and the claims, a solid line indicates a bond, and an arrow indicates that the bond may be dative.

Neutral ligands are defined as ligands that are neutral, with respect to charge, when formally removed from the metal in their closed shell electronic state. Neutral ligands contain at least one lone pair of electrons, pi-bond or sigma bond that are capable of binding to the transition metal. Neutral ligands may also be polydentate when more than one Neutral ligand is connected via a bond or a hydrocarbyl, substituted hydrocarbyl or a functional group tether. A Neutral ligand may be a substituent of another metal complex, either the same or different, such that multiple complexes are bound together.

Anionic ligands are defined as ligands that are anionic, with respect to charge, when formally removed from the metal in their closed shell electronic state. Anionic ligands include hydride, halide, hydrocarbyl, substituted hydrocarbyl or functional group. Non-limiting examples of anionic ligands include hydride, fluoride, chloride, bromide, iodide, alkyl, aryl, alkenyl, alkynyl, allyl, benzyl, acyl, trimethylsilyl. Anionic ligands may also be polydentate when more than one anionic ligand is connected via a bond or a hydrocarbyl, substituted hydrocarbyl or a functional group tether. An anionic ligand may be a substituent of another metal complex, either the same or different, such that multiple complexes are bound together. A mono-anionic ligand is defined to be an anionic ligand that has a −1 charge. A di-anionic ligand is defined to be an anionic ligand that has a −2 charge.

The terms "hydrocarbyl radical," "hydrocarbyl" and "hydrocarbyl group" are used interchangeably throughout this document. Likewise the terms "group" and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic, and include substituted hydrocarbyl radicals, halocarbyl radicals, and substituted halocarbyl radicals, silylcarbyl radicals, and germylcarbyl radicals as these terms are defined below.

Substituted hydrocarbyl radicals are radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-hydrocarbon atom or group has been inserted within the hydrocarbyl radical, such as O, S, Se, Te, $NR^*$, $PR^*$, $AsR^*$, $SbR^*$, $BR^*$, $SiR^*_2$, $GeR^*_2$, $SnR^*_2$, $PbR^*_2$ and the like, where $R^*$ is independently a hydrocarbyl or halocarbyl radical.

Halocarbyl radicals are radicals in which one or more hydrocarbyl hydrogen atoms have been substituted with at least one halogen (e.g. F, Cl, Br, I) or halogen-containing group (e.g. $CF_3$).

Substituted halocarbyl radicals are radicals in which at least one halocarbyl hydrogen or halogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$ and the like or where at least one non-carbon atom or group has been inserted within the halocarbyl radical such as O, S, Se, Te, $NR^*$, $PR^*$, $AsR^*$, $SbR^*$, $BR^*$, $SiR^*_2$, $GeR^*_2$, $SnR^*_2$, $PbR^*_2$ and the like where $R^*$ is independently a hydrocarbyl or halocarbyl radical provided that at least one halogen atom remains on the original halocarbyl radical.

Silylcarbyl radicals (also called silylcarbyls) are groups in which the silyl functionality is bonded directly to the indicated atom or atoms. Examples include $SiH_3$, $SiH_2R^*$, $SiHR^*_2$, $SiR^*_3$, $SiH_2(OR^*)$, $SiH(OR^*)_2$, $Si(OR^*)_3$, $SiH_2(NR^*_2)$, $SiH(NR^*_2)_2$, $Si(NR^*_2)_3$, and the like where $R^*$ is independently a hydrocarbyl or halocarbyl radical as defined above and two or more $R^*$ may join together to form a substituted or unsubstituted saturated, partially unsaturated or aromatic cyclic or polycyclic ring structure.

Polar radicals or polar groups are groups in which the heteroatom functionality is bonded directly to the indicated atom or atoms. They include heteroatoms of groups 1-17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 14) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica. Preferred examples of polar groups include $NR^*_2$, $OR^*$, $SeR^*$, $TeR^*$, $PR^*_2$, $AsR^*_2$, $SbR^*_2$, $SR^*$, $BR^*_2$, $SnR^*_3$, $PbR^*_3$ and the like where $R^*$ is independently a hydrocarbyl, substituted hydrocarbyl, halocarbyl or substituted halocarbyl radical as defined above and two $R^*$ may join together to form a substituted or unsubstituted saturated, partially unsaturated or aromatic cyclic or polycyclic ring structure.

In some embodiments, the hydrocarbyl radical is independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl and triacontyl. Also included are isomers of saturated, partially unsaturated and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this disclosure, when a radical is listed, it indicates that radical type and all other radicals formed when that radical type is subjected to the substitutions defined above. Alkyl and alkenyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compound having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

In the context of this document, "homopolymerization" would produce a polymer made from one monomer. For example, homopolymerization of propylene would produce homopolypropylene, also called polypropylene. It should be noted, however, that some of the catalysts of this invention homopolymerize ethylene or propylene to non-traditional "polyethylene" and "polypropylene" structures, respectively. Likewise, "copolymerization" would produce polymers with more than one monomer type. For example, propylene copolymers include polymers of propylene with other a-olefins, cyclic olefins and diolefins, vinylaromatic olefins, a-olefinic diolefins, substituted ax-olefins, and/or acetylenically unsaturated monomers. Non-limiting examples of α-olefins include 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane. Non-limiting examples of vinylaromatic olefins include styrene, para-methylstyrene, para-t-butylstyrene, vinylnaphthylene, vinyltoluene, and divinylbenzene. Non-limiting examples of a-olefinic dienes include 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1,11-dodecene, 1,13-tetradecene and 9-methyl-1,9-decadiene.

Substituted α-olefins (also called functional group containing α-olefins) include those containing at least one non-carbon Group 13 to 17 atom bound to a carbon atom of the substituted α-olefin where such substitution if silicon may be adjacent to the double bond or terminal to the double bond, or anywhere in between, and where inclusion of non-carbon and -silicon atoms such as for example B, O, S, Se, Te, N, P, Ge, Sn, Pb, As, F, Cl, Br, or I, are contemplated, where such non-carbon or -silicon moieties are sufficiently far removed from the double bond so as not to interfere with the coordination polymerization reaction with the catalyst and so to retain the generally hydrocarbyl characteristic. By being sufficiently far removed from the double bond we intend that the number of carbon atoms, or the number of carbon and silicon atoms, separating the double bond and the non-carbon or -silicon moiety may be 6 or greater, e.g. 7, or 8, or 9, or 10, or 11, or 12, or 13, or 14 or more. The number of such carbon atoms, or carbon and silicon atoms, is counted from immediately adjacent to the double bond to immediately adjacent to the non-carbon or -silicon moiety. Examples include allyltrimethylsilane, divinylsilane, 8,8,8-trifluoro-1-octene, 8-methoxyoct-1-ene, 8-methylsulfanyloct-1-ene, 8-dimethylaminooct-1-ene, or combinations thereof. The use of functional group-containing α-olefins where the functional group is closer to the double bond is also within the scope of embodiments of the invention when such olefins may be incorporated in the same manner as are their α-olefin analogs. See, "Metallocene Catalysts and Borane Reagents in The Block/Graft Reactions of Polyolefins", T. C. Chung, et al, *Polym. Mater. Sci. Eng.*, v. 73, p. 463 (1995), and the masked α-olefin monomers of U.S. Pat. No. 5,153,282. Such monomers permit the preparation of both functional-group containing copolymers capable of subsequent derivatization, and of functional macromers which may be used as graft and block type polymeric segments. All documents cited herein are incorporated by reference for purposes of all jurisdictions where such practice is allowed. Copolymerization can also incorporate α-olefinic macromonomers of up to 2000 mer units.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polypropylene would be propylene.

The terms "catalyst" and "catalyst compound" are defined to mean a compound capable of initiating catalysis. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. The term "catalyst system" is defined to mean: 1) a catalyst precursor/activator pair, and or 2) a catalyst compound capable of intitating catalysis without an activator. When "catalyst system" is used to describe such a pair before activation, it means the unactivated catalyst (pre-catalyst) together with an activator and, optionally, a co-activator. When it is used to describe such a pair after activation, it means the activated catalyst and the activator or other charge-balancing moiety.

The catalyst compound may be neutral as in a pre-catalyst or a catalyst system not requiring an activator, or may be a charged species with a counter ion as in an activated catalyst system.

The terms "activator" and "cocatalyst" are used interchangeably herein. A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator in order to form an active catalyst. In some embodiments a co-activator can be premixed with the transition metal compound to form an alkylated transition metal compound, also referred to as an alkylated invention compound.

Noncoordinating anion (NCA) is defined to mean an anion either that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon.

A stoichiometric activator can be either neutral or ionic. The terms ionic activator, and stoichiometric ionic activator can be used interchangeably. Likewise, the terms neutral stoichiometric activator, and Lewis acid activator can be used interchangeably.

For purposes of this invention and the claims thereto, in describing a ligand, a terminal nitrogen atom, is a nitrogen atom that is indirectly bonded to only one other nitrogen atom. A central nitrogen atom is a nitrogen atom that is indirectly bonded to at least one other nitrogen atom and at least one oxygen atom. A terminal oxygen atom is an oxygen atom that is indirectly bonded to only the central nitrogen atom. An example is illustrated below:

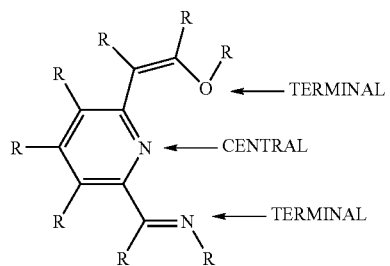
This invention further relates to transition metal compounds represented by formulae 1-10.
Formula 1:
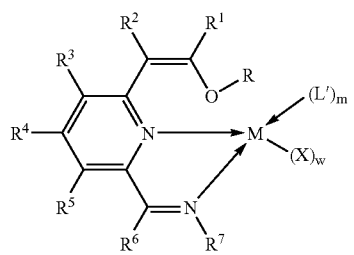
Formula 2:
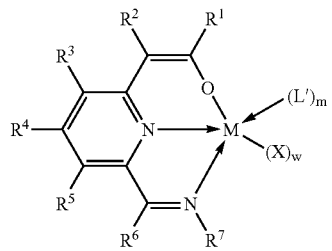
Formula 3:
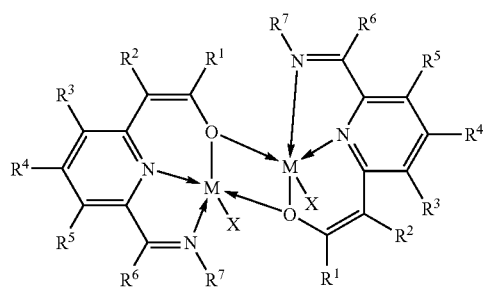
Formula 4:
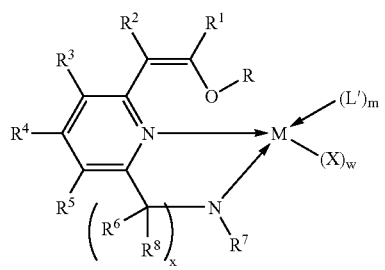
Formula 5:
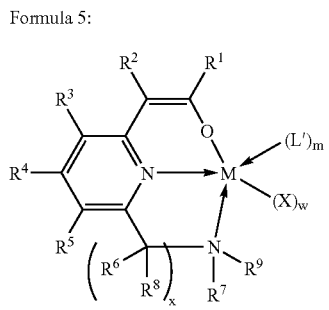
Formula 6:
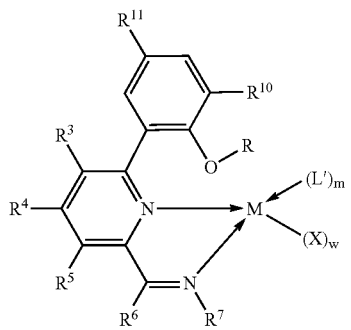
Formula 7:
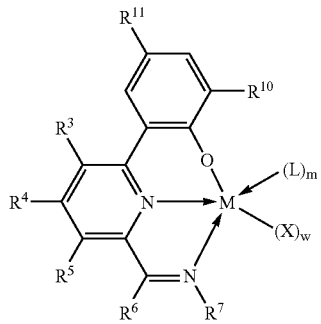
Formula 8:
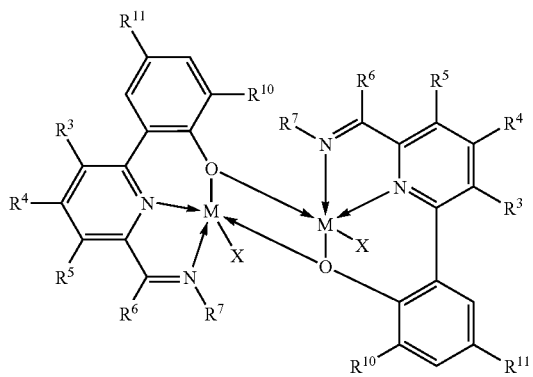

Formula 9:

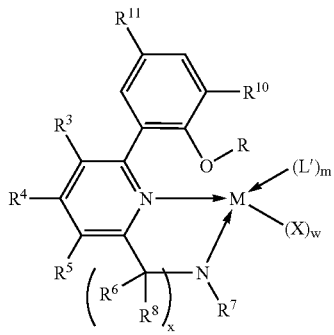

Formula 10:

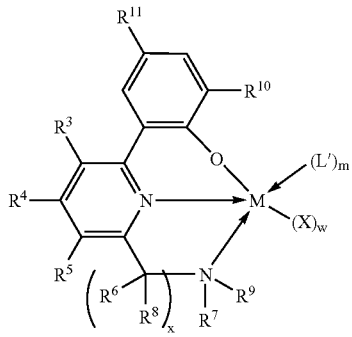

wherein each M is, independently, a group 9, 10, or 11 transition metal, preferably a group 9 or 10 transition metal, preferably cobalt, nickel or palladium;

N is nitrogen;

O is oxygen;

w is 1, 2, or 3;

each X is, independently, a hydride, a halogen, a hydrocarbyl, a substituted hydrocarbyl, a halocarbyl, or a substituted halocarbyl;

additionally, X may independently be selected from halogen, alkoxide, aryloxide, amide, phosphide, or other anionic ligand when Lewis-acid activators (such as methylalumoxane, aluminum alkyls, alkylaluminum alkoxides) or alkylaluminum halides (capable of donating a hydride, hydrocarbyl, substituted hydrocarbyl, halocarbyl or substituted halocarbyl X ligand to the transition metal component) are used, or when an ionic activator is capable of extracting X, provided that the resulting activated catalyst contains as least one M-H or M-C bond into which an olefin can insert;

each R is, independently, hydrogen, or a hydrocarbyl, a substituted hydrocarbyl, a halocarbyl, a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;

each $R_1$ and $R^2$ is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl; or independently, may join together to form a $C_4$ to $C_{62}$ cyclic or polycyclic ring structure;

each $R^3$, $R^4$, $R^5$, is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ $C_{10}$ hydrocarbyl, a C, to $C_{10}$ substituted hydrocarbyl, a $C_1$ $C_{10}$ halocarbyl, or a $C_1$ $C_{10}$ substituted halocarbyl; or independently, may join together to form a $C_4$ to $C_{62}$ cyclic or polycyclic ring structure;

each $R^6$ is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ $C_{10}$ hydrocarbyl, a $C_1$ $C_{10}$ substituted hydrocarbyl, a $C_1$ to $C_{10}$ halocarbyl, or a $C_1$ to $C_{10}$ substituted halocarbyl;

each $R^7$ and $R^9$ is, independently, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;

each $R^8$ is, independently, a hydrogen, a hydrocarbyl, a substituted hydrocarbyl, a halocarbyl, or a substituted halocarbyl, preferably, a $C_1$ to $C_{30}$ hydrocarbyl, a $C_1$ to $C_{30}$ substituted hydrocarbyl, a $C_1$ to $C_{30}$ halocarbyl, or a $C_1$ to $C_{30}$ substituted halocarbyl, more preferably a $C_1$ to $C_{10}$ hydrocarbyl, a $C_1$ to $C_{10}$ substituted hydrocarbyl, a $C_1$ to $C_{10}$ halocarbyl, or a $C_1$ to $C_{10}$ substituted halocarbyl;

each $R^{10}$ is, independently, a hydrocarbyl, a substituted hydrocarbyl, a halocarbyl, or a substituted halocarbyl;

each $R^{11}$ is, independently, a hydrocarbyl, a substituted hydrocarbyl, a halocarbyl, a substituted halocarbyl or a group selected from NO2, sulfonate, halo, carboxyl, sulfonyl ester, a carboxylic ester group, or a perfluoroalkyl group; and each x is, independently, 1, 2, 3 or 4, preferably, x is 1;

L' is a neutral ligand bonded to M that may include molecules such as but not limited to acetonitrile, diethyl ether, tetrahydrofuran, dimethylaniline, trimethylamine, tributylamine, trimethylphosphine, triphenylphosphine lithium chloride, ethylene, propylene, butene, octene, styrene, and the like; and m is 0, 1 or 2 and indicates the absence or presence of L'.

In a preferred embodiment the halocarbyls are fluorocarbyls and the substituted halocarbyls are substituted fluorocarbyls.

To illustrate members of the transition metal catalyst compounds useful in this invention, select any combination of the species listed in Table 1.

TABLE I

| R', R¹, R², R³, R⁴, R⁷ R⁵, R⁶, R¹⁰, R¹¹ | | X | M | L' |
|---|---|---|---|---|
| Hydrogen | Propyl | Chloride | nickel | acetonitrile |
| Methyl | Butyl | Bromide | copper | diethyl ether |
| Ethyl | Pentyl | Iodide | cobalt | tetrahydrofuran |
| Propyl | Hexyl | Methyl | rhodium | furan |
| Butyl | Heptyl | Ethyl | iridium | thiofuran |
| Pentyl | Octyl | Propyl | palladium | chromane |
| Hexyl | Nonyl | Butyl | platinum | isochromane |
| Heptyl | Decyl | Pentyl | silver | thiochromane |
| Octyl | Undecyl | Hexyl | gold | thioisochromane |
| Nonyl | Dodecyl | Heptyl | | quinuclidine |
| decyl | Tridecyl | Octyl | | benzofuran |
| undecyl | Tetradecyl | Nonyl | | chromene |
| dodecyl | Octacosyl | Decyl | | isobenzofuran |
| tridecyl | Nonacosyl | Undecyl | | isoquinoline |
| tetradecyl | Triacontyl | Dodecyl | | oxazole |
| octacosyl | Cyclohexyl | Tridecyl | | phenanthridine |
| nonacosyl | Cyclopentyl | Tetradecyl | | pyran |
| triacontyl | Cycloheptyl | Pentadecyl | | pyridine |
| cyclohexyl | Cyclooctyl | Hexadecyl | | quinoline |
| cyclopentyl | Cyclodecyl | Heptadecyl | | selenophene |
| cycloheptyl | Cyclododecyl | Octadecyl | | thiophene |
| cyclooctyl | Naphthyl | Nonadecyl | | trimethylamine |
| cyclodecyl | Phenyl | Eicosyl | | triethylamine |
| cyclododecyl | Tolyl | Heneicosyl | | tributylamine |
| naphthyl | Benzyl | Docosyl | | dimethylaniline |
| phenyl | Phenethyl | Tricosyl | | trimethylphosphine |
| tolyl | Dimethylphenyl | Tetracosyl | | triphenylphosphine |
| benzyl | Trimethylphenyl | Pentacosyl | | ethylene |
| phenethyl | Methylphenyl | Hexacosyl | | propylene |
| dimethylphenyl | Ethylphenyl | Heptacosyl | | butene |
| diethylphenyl | Diethylphenyl | Octacosyl | | hexene |
| anthracenyl | Triethylphenyl | Nonacosyl | | octene |
| adamantyl | Propylphenyl | Triacontyl | | cyclohexene |
| norbornyl | Dipropylphenyl | Hydride | | vinylcyclohexene |
| CF₃ | Tripropylphenyl | Phenyl | | benzene |
| NO₂ | Methylethylphenyl | Benzyl | | styrene |
| t-butyl | Dibutylphenyl | Phenethyl | | methylstyrene |
| i-propyl | Butylphenyl | Tolyl | | |
| naphthyl | | Methoxy | | |
| fluoride | | Ethoxy | | |
| | | Propoxy | | |
| | | Butoxy | | |
| | | Dimethylamido | | |
| | | Diethylamido | | |
| | | methylethylamido | | |
| | | phenoxy | | |
| | | benzoxy | | |
| | | allyl | | |

A selection of catalyst precursors is detailed below. These precursors are by way of an example only and are not intended to list every catalyst precursor that is within the scope of the invention:

[2-acetyl(2,6-diisopropylanil)-6-phenyl(2'-methoxy)-pyridine]cobalt dichloride

[2-acetyl(2,6-diisopropylanil)-6-phenyl(2'-methoxy)-pyridine]nickel dichloride

[2-acetyl(2,6-diisopropylanil)-6-phenyl(2'-methoxy)-pyridine]copper dichloride

[2-acetyl(2,4,6-trimethylanil)-6-phenyl(2'-methoxy)-pyridine]cobalt dichloride

[2-acetyl(2,4,6-trimethylanil)-6-phenyl(2'-methoxy)-pyridine]nickel dichloride

[2-acetyl(2,4,6-trimethylanil)-6-phenyl(2'-methoxy)-pyridine]copper dichloride

[2-acetyl(2,3,4,5,6-pentafluoroanil)-6-phenyl(2'-methoxy)-pyridine]cobalt dichloride

[2-acetyl(2,3,4,5,6-pentafluoroanil)-6-phenyl(2'-methoxy)-pyridine]nickel dichloride

[2-acetyl(2,3,4,5,6-pentafluoroanil)-6-phenyl(2'-methoxy)-pyridine]copper dichloride

[2-acetyl(2,6-diisopropylanil)-6-phenyl(2'-methoxy,3'-phenyl)-pyridine]cobalt dichloride

[2-acetyl(2,6-diisopropylanil)-6-phenyl(2'-methoxy,3'-phenyl)-pyridine]nickel dichloride

[2-acetyl(2,6-diisopropylanil)-6-phenyl(2'-methoxy,3'-phenyl)-pyridine]copper dichloride

[2-acetyl(2,4,6-trimethylanil)-6-phenyl(2'-methoxy,3'-phenyl)-pyridine]cobalt dichloride

[2-acetyl(2,4,6-trimethylanil)-6-phenyl(2'-methoxy,3'-phenyl)-pyridine]nickel dichloride

[2-acetyl(2,4,6-trimethylanil)-6-phenyl(2'-methoxy,3'-phenyl)-pyridine]copper dichloride

[2-acetyl(2,3,4,5,6-pentafluoroanil)-6-phenyl(2'-methoxy,3'-phenyl)-pyridine]cobalt dichloride

[2-acetyl(2,3,4,5,6-pentafluoroanil)-6-phenyl(2'-methoxy,3'-phenyl)-pyridine]nickel dichloride

[2-acetyl(2,3,4,5,6-pentafluoroanil)-6-phenyl(2'-methoxy,3'-phenyl)-pyridine]copper dichloride

[2-acetyl(2,6-diisopropylanil)-6-phenyl(2'-methoxy,3'-t-butyl)-pyridine]cobalt dichloride
[2-acetyl(2,6-diisopropylanil)-6-phenyl(2'-methoxy,3'-t-butyl)-pyridine]nickel dichloride
[2-acetyl(2,6-diisopropylanil)-6-phenyl(2'-methoxy,3'-t-butyl)-pyridine]copper dichloride
[2-acetyl(2,4,6-trimethylanil)-6-phenyl(2'-methoxy,3'-t-butyl)-pyridine]cobalt dichloride
[2-acetyl(2,4,6-trimethylanil)-6-phenyl(2'-methoxy,3'-t-butyl)-pyridine]nickel dichloride
[2-acetyl(2,4,6-trimethylanil)-6-phenyl(2'-methoxy,3'-t-butyl)-pyridine]copper dichloride
[2-acetyl(2,3,4,5,6-pentafluoroanil)-6-phenyl(2'-methoxy,3'-t-butyl)-pyridine]cobalt dichloride
[2-acetyl(2,3,4,5,6-pentafluoroanil)-6-phenyl(2'-methoxy,3'-t-butyl)-pyridine]nickel dichloride
[2-acetyl(2,3,4,5,6-pentafluoroanil)-6-phenyl(2'-methoxy,3'-t-butyl)-pyridine]copper dichloride
[2-acetyl(2,6-diisopropylanil)-6-phenyl(2'-hydroxy)-pyridine]cobalt dichloride
[2-acetyl(2,6-diisopropylanil)-6-phenyl((2'-hydroxy)-pyridine]nickel dichloride
[2-acetyl(2,6-diisopropylanil)-6-phenyl(2'-hydroxy)-pyridine]copper dichloride
[2-acetyl(2,4,6-trimethylanil)-6-phenyl(2'-hydroxy)-pyridine]cobalt dichloride
[2-acetyl(2,4,6-trimethylanil)-6-phenyl(2'-hydroxy)-pyridine]nickel dichloride
[2-acetyl(2,4,6-trimethylanil)-6-phenyl(2'-hydroxy)-pyridine]copper dichloride
[2-acetyl(2,3,4,5,6-pentafluoroanil)-6-phenyl(2'-hydroxy)-pyridine]cobalt dichloride
[2-acetyl(2,3,4,5,6-pentafluoroanil)-6-phenyl(2'-hydroxy)-pyridine]nickel dichloride Invention catalyst systems can use transition metal catalyst precursors that have a 2+ oxidation state as the additional olefin polymerization catalyst. Typical $Ni^{2+}$ and $Pd^{2+}$ complexes are diimines, see "New Pd(II)- and Ni(II)-Based Catalysts for Polymerization of Ethylene and α-Olefins", M. Brookhart, et al, *J. Am. Chem. Soc.*, 1995, 117, 6414-6415, WO 96/23010 and WO 97/02298. See additionally the related bis(imino) Group 8 and 9 organometallic compounds described by V. C. Gibson and others in "Novel olefin polymerization catalysts based on iron and cobalt", *Chem. Commun.*, 849-850, 1998.

For a review of other potential catalysts used in combination or series with the invention catalysts, see S. D. Ittel and L. K. Johnson, Chem. Rev. 2000, 1000, 1169 and V. C. Gibson and S. K. Spitzmesser, Chem. Rev. 2003, 103, 283.

2. Activators and Catalyst Activation

Optionally, the polymerization catalyst utilized in the polymerization processes of the present invention comprises a metal complex comprising a metal, which optionally is activated by an activator, described in more detail below. The activator optionally is selected from the group consisting of methyl alumoxane (MAO), and a perfluoro tetraphenylborate salt.

The catalyst precursors, when activated by a commonly known activator such as methyl alumoxane, form active catalysts for the polymerization or oligomerization of olefins. Activators that may be used include alumoxanes such as methyl alumoxane, modified methyl alumoxane, ethyl alumoxane, iso-butyl alumoxane and the like; Lewis acid activators include triphenyl boron, tris-perfluorophenyl boron, tris-perfluorophenyl aluminum and the like; Ionic activators include dimethylanilinium tetrakis perfluorophenyl borate, triphenyl carbonium tetrakis perfluorophenyl borate, dimethylanilinium tetrakis perfluorophenyl aluminate, and the like.

A co-activator is a compound capable of alkylating the transition metal complex, such that when used in combination with an activator, an active catalyst is formed. Co-activators include alumoxanes such as methyl alumoxane, modified alumoxanes such as modified methyl alumoxane, and aluminum alkyls such trimethyl aluminum, tri-isobutyl aluminum, triethyl aluminum, and tri-isopropyl aluminum. Co-activators are typically only used in combination with Lewis acid activators and ionic activators when the pre-catalyst is not a dihydrocarbyl or dihydride complex.

The alumoxane component useful as an activator typically is an oligomeric aluminum compound represented by the general formula $(R^x—Al—O)_n$, which is a cyclic compound, or $R^x(R^x—Al—O)_n AlR^x{}_2$, which is a linear compound. In the general alumoxane formula, $R^x$ is independently a $C_1$-$C_{20}$ alkyl radical, for example, methyl, ethyl, propyl, butyl, pentyl, isomers thereof, and the like, and "n" is an integer from 1-50. Most preferably, $R^x$ is methyl and "n" is at least 4. Methyl alumoxane and modified methyl alumoxanes are most preferred. For further descriptions see, EP 0 279 586, EP 0 594 218, EP 0 561 476, WO94/10180 and U.S. Pat. Nos. 4,665,208, 4,874,734, 4,908,463, 4,924,018, 4,952,540, 4,968,827, 5,041,584, 5,091,352, 5,103,031, 5,157,137, 5,204,419, 5,206,199, 5,235,081, 5,248,801, 5,329,032, 5,391,793, and 5,416,229.

When an alumoxane or modified alumoxane is used, the catalyst-precursor-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-catalyst-precursor ratio is 1:1 molar ratio.

Ionic activators (at times used in combination with a co-activator) may be used in the practice of this invention. Preferably, discrete ionic activators such as [Me$_2$PhNH][B(C$_6$F$_5$)$_4$], [Ph$_3$C][B(C$_6$F$_5$)$_4$], [Me$_2$PhNH][B((C$_6$H$_3$-3,5-(CF$_3$)$_2$))$_4$], [Ph$_3$C][B((C$_6$H$_3$-3,5-(CF$_3$)$_2$))$_4$], [NH$_4$][B(C$_6$H$_5$)$_4$] or Lewis acidic activators such as B(C$_6$F$_5$)$_3$ or B(C$_6$H$_5$)$_3$ can be used. Preferred co-activators, when used, are alumoxanes such as methyl alumoxane, modified alumoxanes such as modified methyl alumoxane, and aluminum alkyls such as tri-isobutyl aluminum, and trimethyl aluminum.

It is within the scope of this invention to use an ionizing or stoichiometric activator, neutral or ionic, such as tri (n-butyl) ammonium tetrakis (pentafluorophenyl) borate, a trisperfluorophenyl boron metalloid precursor or a trisperfluoronaphthyl boron metalloid precursor, polyhalogenated heteroborane anions (WO 98/43983), boric acid (U.S. Pat. No. 5,942,459) or combination thereof.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a transition metal compound with an activator, such as $B(C_6F_6)_3$, which upon reaction with the hydrolyzable ligand (X') of the transition metal compound forms an anion, such as $([B(C_6F_5)_3(X')]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention comprise a cation, which is preferably a Bronsted acid capable of donating a proton, and a compatible non-coordinating anion which anion is relatively large (bulky), capable of stabilizing the active catalyst species which is formed when the two compounds are combined and said anion will be sufficiently labile to be displaced by olefinic diolefinic and acetylenically unsaturated substrates or other neutral Lewis bases such as ethers, nitriles and the like. Two classes of compatible non-coordinating anions have been disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes.

In a preferred embodiment, the stoichiometric activators include a cation and an anion component, and may be represented by the following formula:

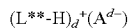

wherein L** is an neutral Lewis base;

H is hydrogen;

(L**-H)$^+$ is a Bronsted acid

A$^{d-}$ is a non-coordinating anion having the charge d-d is an integer from 1 to 3.

The cation component, (L**-H)d+ may include Bronsted acids such as protons or protonated Lewis bases or reducible Lewis acids capable of protonating or abstracting a moiety, such as an alkyl or aryl, from the pre-catalyst after alkylation.

The activating cation (L-H)$_d^+$ may be a Bronsted acid, capable of donating a proton to the alkylated transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether, diethyl ether, tetrahydrofuran and dioxane, sulfoniums from thioethers, such as diethyl thioethers and tetrahydrothiophene, and mixtures thereof. The activating cation (L-H)$_d^+$ may also be a moiety such as silver, tropylium, carbeniums, ferroceniums and mixtures, preferably carboniums and ferroceniums; most preferably triphenyl carbonium.

The anion component A$^{d-}$ include those having the formula [M$^{k+}$Q$_n$]$^{d-}$ wherein k is an integer from 1 to 3; n is an integer from 2-6; n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable A$^{d-}$ also include diboron compounds as disclosed in U.S. Pat. No. 5,447,895, which is fully incorporated herein by reference.

Illustrative, but not limiting examples of boron compounds which may be used as an activating cocatalyst in combination with a co-activator in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(tert-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl(tert-butyl)ammonium tetrakis-(2,3,4,6-,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(tert-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(tert-butyl)ammonium tetrakis(perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(tert-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl)phenyl)borate, and dialkyl ammonium salts such as: di-(iso-propyl) ammonium tetrakis(pentafluorophenyl)borate, and dicyclohexylammonium tetrakis(pentafluorophenyl)borate; and other salts such as tri(o-tolyl)phosphonium tetrakis (pentafluorophenyl)borate, tri(2,6-dimethylphenyl)phosphonium tetrakis(pentafluorophenyl)borate, tropillium tetraphenylborate, triphenylcarbenium tetraphenylborate, triphenylphosphonium tetraphenylborate, triethylsilylium tetraphenylborate, benzene(diazonium)tetraphenylborate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium) tetrakis(pentafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis (perfluoronaphthyl)borate, tropillium tetrakis (perfluorobiphenyl)borate, triphenylcarbenium tetrakis (perfluorobiphenyl)borate, triphenylphosphonium tetrakis (perfluorobiphenyl)borate, triethylsilylium tetrakis (perfluorobiphenyl)borate, benzene(diazonium) tetrakis (perfluorobiphenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, and benzene(diazonium) tetrakis(3,5-bis(trifluoromethyl)phenyl)borate.

Most preferably, the ionic stoichiometric activator ($L^{**}$-$H)_d^+(A^{d-})$ is N,N-dimethylanilinium tetrakis(perfluorophenyl)borate, N,N-dimethylanilinium tetrakis(perfluoronaphthyl)borate, N,N-dimethylanilinium tetrakis (perfluorobiphenyl)borate, N,N-dimethylanilinium tetrakis (3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis (3,5-bis(trifluoromethyl)phenyl)borate, or triphenylcarbenium tetra(perfluorophenyl)borate.

Invention catalyst precursors can also be activated with cocatalysts or activators that comprise non-coordinating anions containing metalloid-free cyclopentadienide ions. These are described in U.S. Patent Publication 2002/0058765 A1, published on 16 May 2002, and for the instant invention, require the addition of a co-activator to the catalyst pre-cursor.

The term "non-coordinating anion" (NCA) means an anion that does not coordinate to the catalyst metal cation or that does coordinate to the metal cation, but only weakly. An NCA coordinates weakly enough that a neutral Lewis base, such as an olefinically or acetylenically unsaturated monomer can displace it from the catalyst center. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal complex cation in the sense of balancing its ionic charge at +1, yet retain sufficient lability to permit displacement by an ethylenically or acetylenically unsaturated monomer during polymerization. These types of cocatalysts sometimes use scavengers such as but not limited to tri-iso-butyl aluminum, tri-n-octyl aluminum, tri-n-hexyl aluminum, triethylaluminum or trimethylaluminum.

The inventive process also can employ cocatalyst compounds or activator compounds that are initially neutral Lewis acids but form a cationic metal complex and a noncoordinating anion, or a zwitterionic complex upon reaction with the alkylated transition metal compounds. The alkylated invention compound is formed from the reaction of the catalyst pre-cursor and the co-activator. For example, tris(pentafluorophenyl) boron or aluminum act to abstract a hydrocarbyl ligand to yield an invention cationic transition metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting formal anionic ligands. See in particular the review article by E. Y.-X. Chen and T. J. Marks, "Cocatalysts for Metal-Catalyzed Olefin Polymerization: Activators, Activation Processes, and Structure-Activity Relationships," Chem. Rev., 100, 1391-1434 (2000).

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation.

When an ionic or neutral stoichiometric activator is used, the catalyst-precursor-to-activator molar ratio is from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2. The catalyst-precursor-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Preferred activators and activator/co-activator combinations include methylalumoxane, modified methylalumoxane, mixtures of methylalumoxane with dimethylanilinium tetrakis(pentafluorophenyl)borate or tris(pentafluorophenyl) boron, and mixtures of trimethyl aluminum with dimethylanilinium tetrakis(pentafluorophenyl)borate or tris(pentafluorophenyl)boron In some embodiments, scavenging compounds are used with stoichiometric activators. Typical aluminum or boron alkyl components useful as scavengers are represented by the general formula $R^xJZ_2$ where J is aluminum or boron, $R^x$ is as previously defined above, and each Z is independently $R^x$ or a different univalent anionic ligand such as halogen (Cl, Br, I), alkoxide (OR$^x$) and the like. Most preferred aluminum alkyls include triethylaluminum, diethylaluminum chloride, tri-iso-butylaluminum, tri-n-octylaluminum, tri-n-hexylaluminum, trimethylaluminum and the like. Preferred boron alkyls include triethylboron. Scavenging compounds may also be alumoxanes and modified alumoxanes including methylalumoxane and modified methylalumoxane.

3. Supported Catalysts

The solubility of invention catalyst precursors allows for the ready preparation of supported catalysts. To prepare uniform supported catalysts, the catalyst or catalyst precursor preferably dissolves in the chosen solvent. The term "uniform supported catalyst" means that the catalyst, or the catalyst precursor and the activator, and or the activated catalyst approach uniform distribution upon the support's accessible surface area, including the interior pore surfaces of porous supports. Some embodiments of supported catalysts prefer uniform supported catalysts; other embodiments show no such preference.

Invention supported catalyst, systems may be prepared by any method effective to support other coordination catalyst systems, effective meaning that the catalyst so prepared can be used for oligomerizing or polymerizing olefin in a heterogenous process. The catalyst precursor, activator, co-activator if needed, suitable solvent, and support may be added in any order or simultaneously.

By one method, the activator, dissolved in an appropriate solvent such as toluene may be stirred with the support material for 1 minute to 10 hours. The total solution volume may be greater than the pore volume of the support, but some embodiments limit the total solution volume below that needed to form a gel or slurry (about 90% to 400%, preferably about 100-200% of the pore volume). The mixture is optionally heated from 30-200° C. during this time. The catalyst precursor may be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution and vacuum dried or evaporation alone removes the solvent.

Alternatively, the catalyst precursor and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The catalyst precursor may also be supported absent the activator; in that case, the activator (and co-activator if needed) is added to a slurry process's liquid phase. For example, a solution of catalyst precursor may be mixed with a support material for a period of about 1 minute to 10 hours. The resulting pre-catalyst mixture may be filtered from the solution and dried under vacuum, or evaporation alone removes the solvent. The total, catalyst-precursor-solution volume may be greater than the support's pore volume, but some embodiments limit the total solution volume below that needed to form a gel or slurry (about 90% to 400%, preferably about 100-200% of the pore volume).

Additionally, two or more different catalyst precursors may be placed on the same support using any of the support methods disclosed above. Likewise, two or more activators or an activator and co-activator may be placed on the same support.

Suitable solid particle supports are typically comprised of polymeric or refractory oxide materials, each being preferably porous. Any support material that has an average particle size greater than 10 µm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Invention catalyst carriers may have a surface area of from 10-700 m$^2$/g, a pore volume of 0.1-4.0 cc/g and an average particle size of 10-500 µm. Some embodiments select a surface area of 50-500 m$^2$/g, a pore volume of 0.5-3.5 cc/g, or an average particle size of 20-200 µm. Other embodiments select a surface area of 100-400 m$^2$/g, a pore volume of 0.8-3.0 cc/g, and an average particle size of 30-100 µm. Invention carriers typically have a pore size of 10-1000 Angstroms, alternatively 50-500 Angstroms, or 75-350 Angstroms.

Invention catalysts are generally deposited on the support at a loading level of 10-100 micromoles of catalyst precursor per gram of solid support; alternately 20-80 micromoles of catalyst precursor per gram of solid support; or 40-60 micromoles of catalyst precursor per gram of support. But greater or lesser values may be used provided that the total amount of solid catalyst precursor does not exceed the support's pore volume.

Invention catalysts can be supported for gas-phase, bulk, or slurry polymerization, or otherwise as needed. Numerous support methods are known for catalysts in the olefin polymerization art, particularly alumoxane-activated catalysts; all are suitable for this invention's broadest practice. See, for example, U.S. Pat. Nos. 5,057,475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582 and 5,466,649, and international publications WO 93/11172 and WO 94/07928.

Having now fully described the invention, it will be appreciated by those skilled in the art that the invention may be performed within a wide range of parameters within what is claimed, without departing from the spirit and scope of the invention.

We claim:

1. A process for producing polypropylene, wherein the process comprises the steps of:
   (a) providing a propylene-containing stream from an oxygenate to olefin reaction system, wherein the propylene-containing stream comprises propylene and at least about 10 wppm oxygenates, based on the total weight of the propylene-containing stream;
   (b) directing the propylene-containing stream to a polymerization zone; and
   (c) contacting the propylene in the propylene-containing stream with a polymerization catalyst in the polymerization zone under conditions effective to polymerize the propylene to form the polypropylene, wherein said catalyst comprises a metal complex comprising a metal selected from Group 6, 7, 8, 9, 10 or 11 of the Periodic Table of the Elements.

2. The process of claim 1, wherein the metal complex is activated by an activator.

3. The process of claim 2, wherein the activator is selected from the group consisting of methyl alumoxane (MAO), and a perfluoro tetraphenylborate salt.

4. The process of claim 1, wherein the metal complex comprises a tridentate ligand.

5. The process of claim 4, wherein the tridentate ligand comprises three nitrogen atoms, which coordinate with the metal.

6. The process of claim 5, wherein at least one of the nitrogen atoms is bonded to a 2,6-diisopropyl phenyl substituent.

7. The process of claim 4, wherein the tridentate ligand comprises two nitrogen atoms and one oxygen atom, and wherein the two nitrogen atoms and the oxygen atom coordinate with the metal.

8. The process of claim 7, wherein at least one of the nitrogen atoms is bonded to a 2,6-diisopropyl phenyl substituent.

9. The process of claim 1, wherein the metal is selected from the group consisting of iron, ruthenium, osmium, hassium, cobalt, rhodium, iridium, meitnerium, nickel, palladium, platinum and darmstadtium.

10. The process of claim 9, wherein the metal is selected from the group consisting of iron, cobalt and nickel.

11. The process of claim 9, wherein the metal is selected from the group consisting of nickel and palladium.

12. The process of claim 1, wherein the metal complex is dispersed in water.

13. The process of claim 1, wherein the oxygenate comprises one or more of methanol, ethanol, dimethyl ether, ethanal, propanal, acetone, isopropyl alcohol and mixtures thereof.

14. The process of claim 1, wherein the propylene-containing stream comprises at least about 1000 wppm oxygenates, based on the total weight of the propylene-containing stream.

15. The process of claim 14, wherein the propylene-containing stream comprises at least about 1 weight percent oxygenates, based on the total weight of the propylene-containing stream.

16. The process of claim 15, wherein the propylene-containing stream comprises at least about 2 weight percent oxygenates, based on the total weight of the propylene-containing stream.

17. The process of claim 16, wherein the propylene-containing stream comprises at least about 5 weight percent oxygenates, based on the total weight of the propylene-containing stream.

18. The process of claim 1, wherein the propylene-containing stream comprises from about 10 wppm to about 10 weight percent oxygenates, based on the total weight of the propylene-containing stream.

19. The process of claim 1, wherein the propylene-containing stream comprises less than about 10 weight percent oxygenates, based on the total weight of the propylene-containing stream.

20. The process of claim 1, wherein the propylene-containing stream comprises less than about 5 wppm water, based on the total weight of the propylene-containing stream.

21. The process of claim 1, wherein the propylene-containing stream is derived from an initial product stream comprising ethylene, propylene, water and the oxygenate.

22. The process of claim 1 wherein the propylene-containing stream is provided by an oxygenate to olefin process comprising the steps of:
   (a) contacting an oxygenate with a molecular sieve catalyst composition in an oxygenate to olefins reaction system under first conditions effective to form an initial product stream comprising ethylene, propylene and an oxygenate; and
   (b) separating the initial product stream into an ethylene-containing stream and a propylene-containing stream, wherein the ethylene-containing stream comprises a weight majority of the ethylene, based on the total weight of the initial product stream, and wherein the propylene-containing stream comprises a weight majority of the propylene, based on the total weight of the propylene-containing stream, and at least a portion of the oxygenate.

23. The process of claim 1 wherein the metal is selected from Group 8, 9 or 10 of the Periodic Table of the Elements.

24. The process of claim 1 wherein the metal is selected from Group 9, 10 or 11 of the Periodic Table of the Elements.

25. A process for producing polypropylene, wherein the process comprises the steps of:
   (a) providing a propylene-containing stream from an oxygenate to olefin reaction system, wherein the propylene-containing stream comprises propylene and at least about 10 wppm oxygenates, based on the total weight of the propylene-containing stream;
   (b) directing the propylene-containing stream to a polymerization zone; and
   (c) contacting the propylene in the propylene-containing stream with a polymerization catalyst in the polymerization zone under conditions effective to polymerize the propylene to form the polypropylene, wherein said catalyst comprises a metal complex comprising a metal selected from Group 11 of the Periodic Table of the Elements.

* * * * *